United States Patent [19]

Skrabal et al.

[11] Patent Number: 5,373,855
[45] Date of Patent: Dec. 20, 1994

[54] TWO-CHANNEL NEEDLE FOR WITHDRAWING BODY FLUIDS

[75] Inventors: Ealko Skrabal, Graz; Erich Kleinhappl, Weinitzen, both of Austria

[73] Assignee: AVL Medical Instruments AG, Schaffhausen, Switzerland

[21] Appl. No.: 117,643

[22] Filed: Sep. 8, 1993

Related U.S. Application Data

[63] Continuation of Ser. No. 723,296, Jun. 28, 1991, abandoned.

[30] Foreign Application Priority Data

Jul. 4, 1990 [AT] Austria ............... A1425/90

[51] Int. Cl.5 .................................. A61B 10/00
[52] U.S. Cl. ................... 128/750; 128/753; 604/44; 604/164
[58] Field of Search ............. 128/753, 754, 752, 751, 128/749, 760, 762, 768; 604/164, 158, 264, 272, 280, 283, 284, 27, 36, 43, 44, 48, 167

[56] References Cited

U.S. PATENT DOCUMENTS

| | | | |
|---|---|---|---|
| 3,606,878 | 9/1971 | Kellogg, Jr. | 128/753 |
| 4,073,297 | 2/1978 | Kopp | 604/164 |
| 4,224,943 | 9/1980 | Johnson et al. | 604/44 |
| 4,249,541 | 2/1981 | Pratt | 128/753 |
| 4,270,535 | 6/1981 | Bogue et al. | 604/164 |
| 4,314,565 | 2/1982 | Lee | 128/753 |
| 4,531,935 | 7/1985 | Berryessa | 604/45 |
| 4,808,156 | 2/1989 | Dean | 604/43 |
| 4,817,631 | 4/1989 | Schnepp-Pesch et al. | 128/753 |
| 4,850,373 | 7/1989 | Zatloukal et al. | 128/749 |
| 4,935,008 | 6/1990 | Lewis, Jr. | 604/52 |
| 4,994,047 | 2/1991 | Walker et al. | 604/264 |
| 5,012,818 | 5/1991 | Joishy | 128/754 |
| 5,120,317 | 6/1992 | Luther | 604/158 |
| 5,156,596 | 10/1992 | Balbierz et al. | 604/164 |

FOREIGN PATENT DOCUMENTS

0191599 8/1986 European Pat. Off.
88/05643 8/1988 WIPO.

Primary Examiner—Stephen C. Pellegrino
Assistant Examiner—Guy V. Tucker
Attorney, Agent, or Firm—Watson, Cole, Grindle & Watson

[57] ABSTRACT

A two-channel sampling needle is designed for withdrawing body fluids, such as blood or tissue fluid, has two essentially parallel cannulas, the first cannula being provided with an insertion needle which may be removed after the sampling needle has been introduced, its sharpened end projecting beyond the end of the first cannula. At the distal end of the sampling needle the second cannula has at least one connecting opening into the first cannula. A mounting part of the sampling needle is provided with fittings for the two cannulas and with a separate opening plugged by a flexible stopper for removal of the insertion needle.

10 Claims, 2 Drawing Sheets

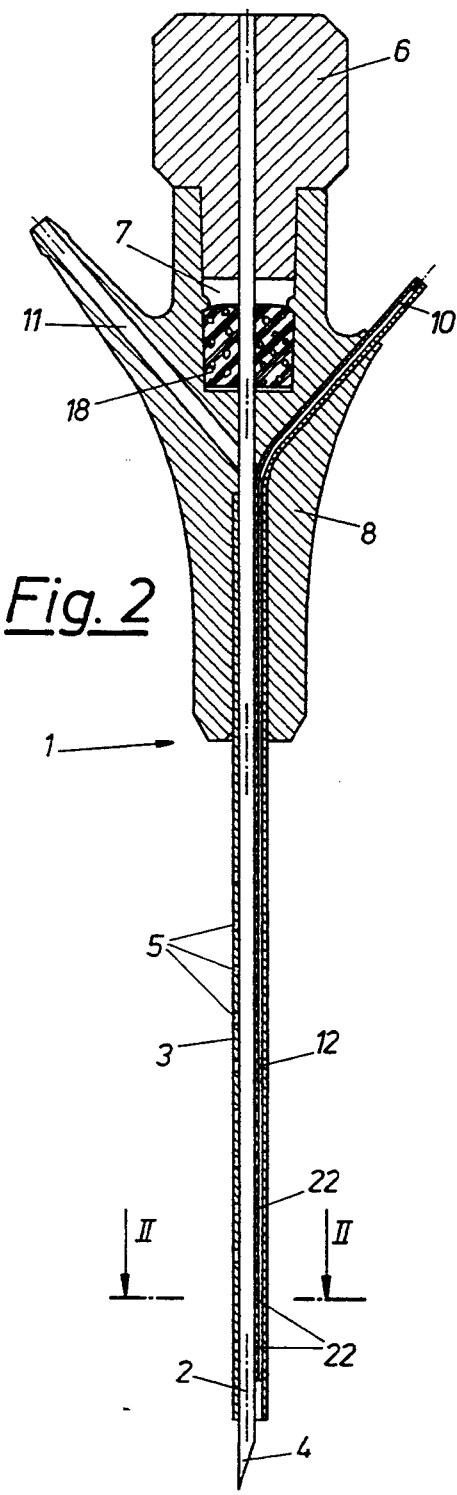
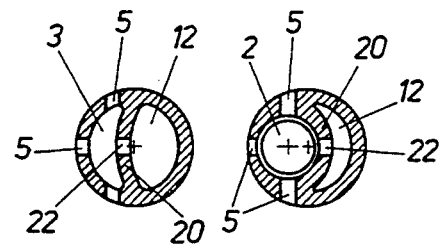
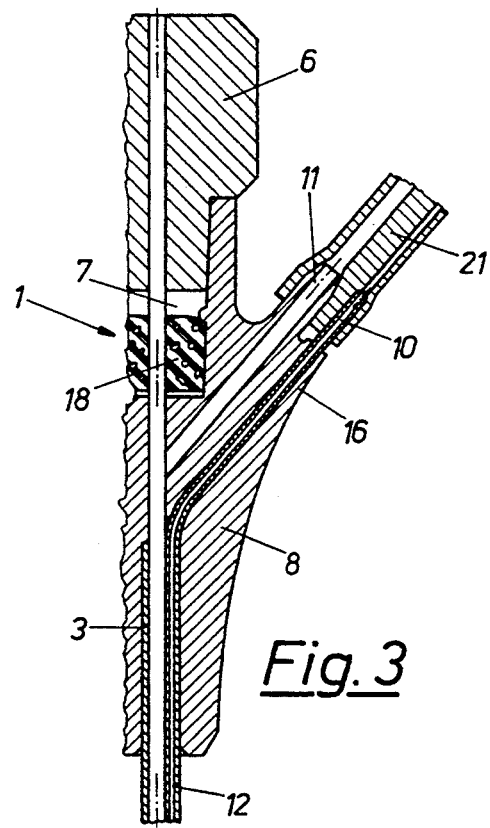

TWO-CHANNEL NEEDLE FOR WITHDRAWING BODY FLUIDS

CROSS REFERENCE TO RELATED APPLICATION

This application is a continuation of application Ser. No. 07/723,296, filed Jun. 28, 1991, now abandoned.

BACKGROUND OF THE INVENTION

This invention relates to a two-channel sampling needle for withdrawing fluids, such as blood or tissue fluid, from a body comprising two essentially parallel flexible cannulas, the first cannula being provided with an insertion needle which may be removed after the sampling needle has been introduced into the body, the sharpened end of this insertion needle projecting beyond the end of the first cannula.

DESCRIPTION OF THE PRIOR ART

In medical applications there are a number of uses for double-channel needles, which are particularly useful if a substance is to be fed into the body through one channel while the other one is required for draining this substance, a reaction product or a body fluid from the body.

In tissue perfusion, for instance, a perfusion fluid is delivered to the tissue through one channel of a two-channel needle, and is subsequently recovered through the other channel after a short equilibration phase. The exterior wall of the needle is provided with openings to increase the area of contact with the tissue.

In WO 88/05643, for instance, several design variants of two-channel needles are disclosed, which essentially comprise two concentric steel tubes, placed one within the other. Two-channel steel needles may be manufactured with comparatively small overall diameters and will help minimize the discomfort involved for the patient, in addition to providing the necessary material strength required for tissue puncturing. Because of the rigidity of the needle, however, they are less comfortable to wear for prolonged periods of time.

WO 88/05643 further discloses a catheter or sampling needle of flexible material, whose inner cannula carries on its outside a number of septums giving a star-shaped cross-section, the capillary spaces between these septums forming the outer cannula of the needle bounded by the adjacent tissue. While the tissue is punctured the flexible catheter is contained in a hollow needle, which is subsequently removed, leaving only the flexible catheter in the tissue. The disadvantages of this design are the increase in overall diameter due to the hollow needle, which will add to the patient's discomfort, and the increase in manipulating efforts required.

In EP-A 0 191 599 a two-channel sampling needle of the type described in the opening paragraph is disclosed, which is only suitable for the purpose of dialysis, however. The openings of the two cannulas are as remote from each other as possible, in order to prevent a quantity of blood introduced into a blood vessel by the dialyzing device from being instantly drained through the second cannula. Besides, a certain amount of manipulation is required to establish a connection with the dialyzing device after the insertion needle has been removed from one of the two cannulas, without risking any contact with blood.

SUMMARY OF THE INVENTION

It is an object of the invention to propose a needle for withdrawing body fluids as described above which will combine a small overall cross-section with increased wearing comfort even for prolonged periods of time, in addition to being suitable for use in tissue perfusion. Besides, manipulation efforts should be reduced and body fluids should be prevented from issuing.

In the invention this object is achieved by providing the second cannula with at least one connecting opening into the first cannula at the distal end of the sampling needle, and by providing a mounting part of the sampling needle with fittings for the two cannulas and with a separate opening for removing the insertion needle, which opening is plugged by a flexible stopper. In this way it will be possible to induce a reversal of flow, for instance, of a perfusion fluid, within the sampling needle itself. Since the mounting part of the sampling needle contains a separate opening plugged by a flexible stopper for removal of the insertion needle, in addition to the fittings for the two cannulas, body fluid will not be able to issue. The necessary material strength required for puncturing is provided by the insertion needle, which may be made of steel, for example, the overall cross-section remaining small as no exterior hollow needle will be needed. After removal of the insertion needle a flexible and resilient two-channel sampling needle will remain which is comfortable to wear. A metal or hard plastic tube could be used as a second or interior cannula, which would be flexible because of its small cross-section and would not enter into contact with the body.

In a first variant of the invention, which is characterized by great ease of handling, that the mounting part contains a cavity in connection with the first cannula, which cavity is plugged by the flexible stopper pierced by the insertion needle, and further the mounting part has a projection with the fittings for the two cannulas, one of these fittings opening into the first cannula and into the cavity in the mounting part, and the other fitting connecting to the second cannula.

In another variant of the invention the cavity in the mounting part is adjusted to approach the interior diameter of the outer plastic cannula with the use of a stepless cone, and the second cannula is located between the insertion needle and the wall of the first cannula. Insertion of the second, inner cannula during manufacture of the needle is facilitated by the conical transition.

In a further enhanced variant of the invention both cannulas are made of plastic, the second cannula being molded integral with the first, and the lumen or interior cross-section of the second cannula extends into that of the first cannula only after the insertion needle has been removed. As long as the insertion needle remains within the sampling needle, the lumen of the second cannula may take the shape of a narrow slit, which will unfold after removal of the insertion needle, in accordance with the different pressures in the two cannulas. It would also be possible, of course, to use double-channel needles whose cross-sections do not undergo variations.

In another preferred variant of the invention the projection is provided with a bore opening into the cavity, into which bore a connecting piece can be inserted so as to be gas-tight, holding the fittings or lines leading to the two cannulas.

According to another feature of the invention the connecting piece with the two fittings is fastened to the projection on the mounting part by means of a threaded part. For this purpose a luer lock is recommended.

The sampling needle of the invention is very well suited for applications in the tissue, if the invention provides for perforations in the wall of the first cannula.

Finally, it is an advantage for special applications of the invention if the wall of the first cannula has a perforation covered by a membrane that is permeable to selected components of the tissue fluid.

For safe handling of the two-channel sampling needle it is proposed by the invention that both fittings be insertable into a coupling element with ingoing and outgoing lines, without any risk of confusion.

BRIEF DESCRIPTION OF THE DRAWINGS

Following is a more detailed description of the invention as illustrated by the attached drawings, in which FIGS. 2, 3 show variants of the invention, FIGS. 4a, 4b show sections along line II—II in FIG. 2.

DETAILED DESCRIPTION OF THE PREFERRED EMBODIMENTS

Figure 1:
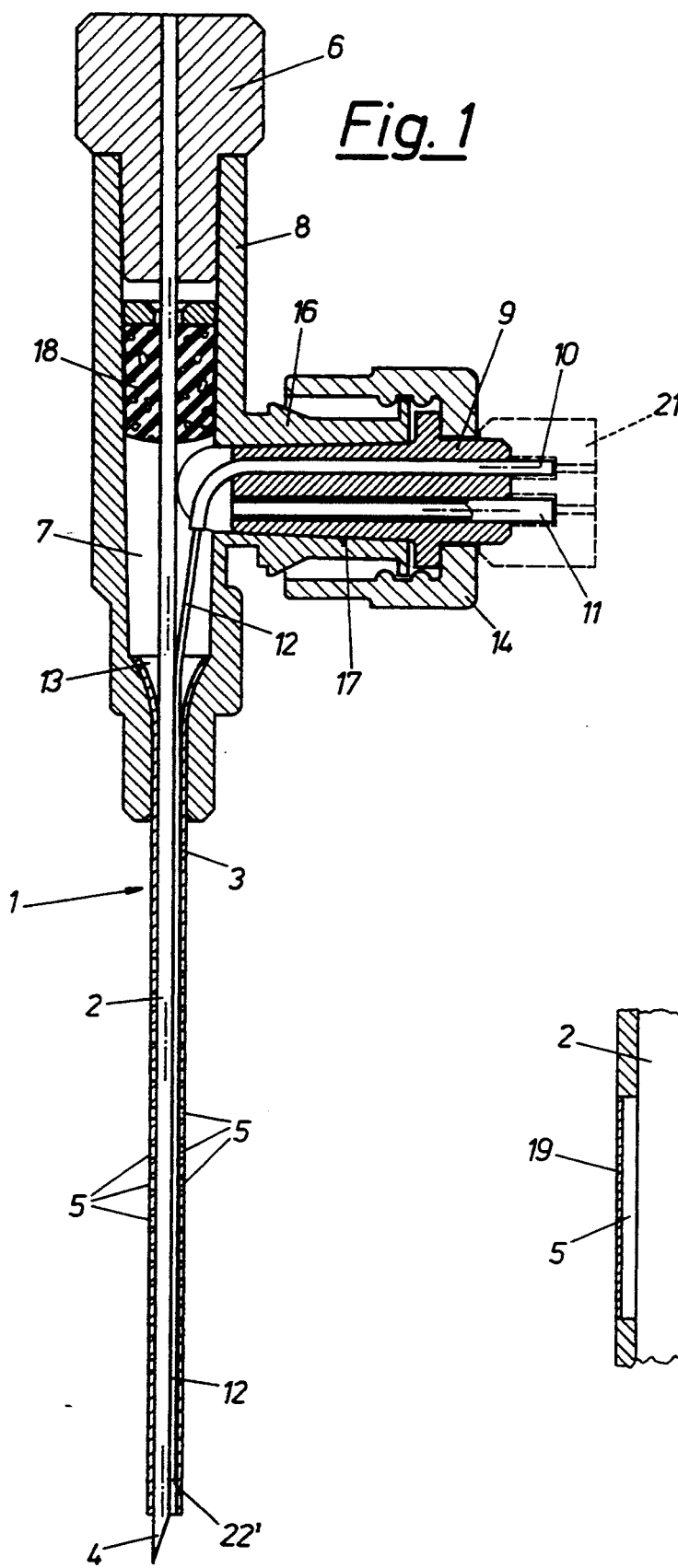
FIG. 1 shows a two-channel sampling needle according to the invention.

The sampling needle 1 shown in FIG. 1 is provided with an insertion needle 2, for instance, a steel needle or a metal pin, which is fitted into a flexible first cannula 3, made of plastic, for example, such that only the sharpened or pointed end 4 of the insertion needle 2 remains uncovered. The wall of the cannula 3 has several perforations 5 distributed over its circumference, through which the perfusion fluid enters into contact with the tissue. At its other end, i.e. remote from the pointed end 4, the insertion needle 2 has a handling knob 6 closing off a cavity 7 in the mounting part 8 of the needle 1. For applications in blood vessels, sampling needles 1 are used whose exterior cannulas 3 do not have any perforations. At the end 4 of the insertion needle 2 the cannula 3 may be tapered to approach the diameter of the insertion needle 2 in order to permit a stepless transition from needle to cannula.

A second, interior cannula 12 is placed between the insertion needle 2 and the first, exterior cannula 3. The use of a stepless cone 13 between the cavity 7 and the exterior cannula 3 will facilitate the insertion of the interior cannula 12 during manufacture of the needle. The interior cannula 12 may be deformed and pressed against the inner wall of the exterior cannula 3, unfolding to its full cross-section only after the insertion needle 2 has been removed, or it may be situated in a groove along the inner wall of the exterior cannula 3. The mounting part 8 is provided with a lateral projection 16 receiving a connecting piece 9 for fittings 10, 11 in a bore 17 connected to the cavity 7. The fitting 10 is directly connected to the second or interior cannula 12 ending shortly before, or flush with, the first or exterior cannula 3. The opening connecting the first and second cannulas has the reference number 22. The interior cannula could be a thin metal tube or a plastic tube with a steel mandrin. The second fitting 11 opens into the cavity 7 in the mounting part 8, and is thus connected to the space between interior and exterior cannula. After its insertion into the lateral projection 16, the connecting piece 9 is fastened by means of a threaded part 14, preferably a luer lock.

It will also be possible, however, to attach the fittings 10 and 11 to the projection 16 itself by potting or bonding.

In the area between the end of the bore 17 opening into the cavity 7 and the handling knob 6 of the insertion needle 2 a flexible stopper 18 is placed, which is pierced by the insertion needle 2. Once the tissue is punctured the insertion needle 2 is withdrawn by its handling knob 6, and the opening in the flexible stopper 18 closes up, such that the latter will automatically seal the cavity 7. After this the sampling needle 1 is ready for instant use.

In the variant shown in FIG. 2 all parts corresponding to those of the variant in FIG. 1 have corresponding reference numbers. In this variant the second plastic cannula 12 is combined with the first cannula 3 to form a one-piece unit, and the second cannula may be located in the wall of the first cannula. According to FIGS. 2 and 3 the fittings 10 and 11 may be directly integrated into the mounting part 8, and are connected to the first and second cannula, i.e., 3 and 12, respectively. According to FIGS. 1 and 3 the fittings 10 and 11 may have a joint coupling element 21 into which the two fittings 10, 11 may be inserted without the risk of confusion on account of their different dimensions and shapes. It will of course be possible to do without a coupling element and use a connecting piece 9 instead, which is integrated with the lines leading to corresponding equipment and evaluation devices.

FIGS. 4a and 4b show sections of one and the same area of the needle tip; 4a including the insertion needle, and 4b showing the same area after removal of the insertion needle, permitting the formerly slit-like or crescent-shaped cross-section of the second cannula to unfold.

The partition 20 between first and second cannula, i.e., 3 and 12, has openings 22 in this area. In the variants according to FIGS. 2 and 3 the wall perforations 5 are not distributed over the entire circumference but only in the area not taken by the second cannula.

Figure 5:
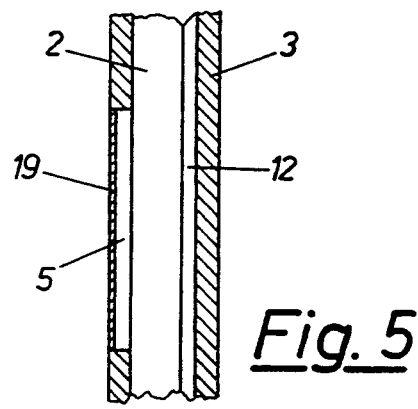
FIG. 5 shows a detail of another variant of the invention.

According to a detail of a variant of the sampling needle 1 which is presented in FIG. 5, the exterior cannula 3 may be provided with only one perforation 5 (or a smaller number of perforations 5), which is covered by a membrane 19 selective for particular sample components.

We claim:

1. A two channel sampling needle device for insertion into a body to withdraw fluids, comprising a mounting part which defines an internal cavity, a flexible first cannula which is supported by said mounting part and extends from a proximal end in communication with said internal cavity to a distal end remote therefrom, said first cannula defining an uninterrupted first lumen, a flexible second cannula which is supported by said mounting part and which extends within said first cannula and in parallel therewith, said second cannula providing a first opening which directly opens into said first lumen near said distal end of said first cannula, a first fitting which is supported by said mounting part and is in communication with said cavity and said first cannula, a second fitting which is supported by said mounting part and is connected to said second cannula, a flexible stopper positioned within said cavity, and an insertion needle having a sharpened end which is extendable through said stopper, said cavity and along said first lumen such that said sharpened end extends beyond said distal end of said first cannula, said insertion needle, after insertion into a body, being withdrawable from said first cannula and said mounting part, wherein perfusion fluid can circulate between said first and second cannula within said needle device.

2. A sampling needle according to claim 1, wherein said mounting part defines a projection containing said first and second fittings.

3. A sampling needle according to claim 2, wherein said mounting part defines a secured opening through which said first cannula extends, wherein said mounting part provides a stepless cone leading from said cavity towards said second opening.

4. A sampling needle according to claim 2, wherein said first and second cannulas are plastic, and wherein said second cannula is one-piece with said first cannula.

5. A sampling needle according to claim 4, wherein said second defines a second lumen, and wherein said second lumen of said second cannula extends into said first lumen of said first after said insertion needle is removed from said first cannula.

6. A sampling needle according to claim 2, including a connecting piece, and wherein said projection defines a bore communicating with said cavity, and wherein said connecting piece is insertable in a gas-tight fashion into said bore, said connecting piece holding said first and second fittings.

7. A sampling needle according to claim 6, including a threaded element for fastening said connecting piece containing said first and second fittings to said projection of said mounting part.

8. A sampling needle according to claim 1, wherein said first cannula includes a wall which has perforation.

9. A sampling needle according to claim 1, wherein said first cannula includes a wall which has perforations covered by a membrane which is permeable to selected components of tissue fluid.

10. A sampling needle according to claim 1, including a coupling element with ingoing and outgoing lines into which said first and second fittings are insertable.

* * * * *

UNITED STATES PATENT AND TRADEMARK OFFICE
CERTIFICATE OF CORRECTION

PATENT NO. : 5,373,855
DATED : December 20, 1994
INVENTOR(S) : Falko SKRABAL et al.

It is certified that error appears in the above-identified patent and that said Letters Patent is hereby corrected as shown below:

ON THE TITLE PAGE:

In the heading, replace with

[75] Inventors: Falko Skrabal, Graz; Erich Kleinhappl, Weinitzen, both of Austria Signed and Sealed this Fourteenth Day of February, 1995

Attest:

BRUCE LEHMAN

Attesting Officer    Commissioner of Patents and Trademarks